(12) United States Patent
Wan et al.

(10) Patent No.: US 6,539,281 B2
(45) Date of Patent: Mar. 25, 2003

(54) ONLINE MEDICINE CABINET

(75) Inventors: Dadong Wan, Palatine, IL (US); Anatole V. Gershman, Chicago, IL (US)

(73) Assignee: Accenture Global Services GmbH (CH)

( * ) Notice: Subject to any disclaimer, the term of this patent is extended or adjusted under 35 U.S.C. 154(b) by 28 days.

(21) Appl. No.: 09/840,248

(22) Filed: Apr. 23, 2001

(65) Prior Publication Data

US 2002/0153411 A1 Oct. 24, 2002

(51) Int. Cl.$^7$ ............................................. G06F 17/00
(52) U.S. Cl. ...................... 700/236; 700/237; 700/244
(58) Field of Search ............................. 700/231, 236, 700/241, 244, 237

(56) References Cited

U.S. PATENT DOCUMENTS

| | | | | |
|---|---|---|---|---|
| 4,275,384 A | * | 6/1981 | Hicks et al. ............. | 340/309.4 |
| 5,597,995 A | * | 1/1997 | Williams et al. ............ | 235/375 |
| 5,905,653 A | * | 5/1999 | Higham et al. ............ | 700/244 |
| 5,930,145 A | * | 7/1999 | Yuyama et al. ............ | 700/231 |
| 6,151,536 A | * | 11/2000 | Arnold et al. ............... | 700/237 |
| 6,181,982 B1 | * | 1/2001 | Yuyama et al. ............ | 700/236 |
| 6,335,907 B1 | * | 1/2002 | Momich et al. ............. | 368/10 |
| 6,339,732 B1 | * | 1/2002 | Phoon et al. ............... | 700/237 |

OTHER PUBLICATIONS

AIM (Automatic Identification Manufacturers), "Radio Frequency Identification—RFID, A basic primer", AIM (Automatic Identification Manufacturers) website, pp. 1–20, Sep. 28, 1999.

AIM (Automatic Identification Manufacturers), "What is Radio Frequency Identification (RFID), ", AIM (Automatic Identification Manufactureres) website, pp. 1–4, May 12, 2000.

AIM (Automatic Identification Manufacturers), "Glossary of Radio Frequency Identification (RFID) terms ", AIM (Automatic Identification Manufacturers) website, pp. 1–10, May 12, 2000.

AIM (Automatic Identification Manufacturers), "Draft Paper on the Characteristics of RFID—Systems", AIM Frequency Forums AIM FF2000:001 Ver 1.0, pp. 1–23, Jul., 2000.

(List continued on next page.)

*Primary Examiner*—Khoi H. Tran
(74) *Attorney, Agent, or Firm*—Banner & Witcoff, Ltd.

(57) ABSTRACT

A medicine cabinet or similar device that assists users in selecting and taking medication. A radio frequency receiver is configured to read information included on radio frequency sensitive labels that are attached to items containing medication in the medicine cabinet. A computer in the medicine cabinet is operatively connected to the radio frequency receiver and also to a wide area network, such as the Internet. The medicine cabinet has a display device that is operatively coupled with the computer and, in the form of a touch screen flat panel, the display device functions to interface the user and the medicine cabinet. The computer is configured to transmit information to the Internet and receives information from websites or additional computers that are coupled to the Internet. Information regarding medications and users as well as vital signs records of the users are stored either in the memory of the medicine cabinet or at a remote location via the connection to the Internet.

21 Claims, 6 Drawing Sheets

OTHER PUBLICATIONS

William Borden, "Panasonic Debuts Web–Based Home Health Care Device", dailynews.yahoo.com, pp. 1–3, May 31, 2000.

Stan Bernard, "Digital Doctoring", www.business 2.0, pp. 1–2, Aug. 22, 2000.

CNNfn Digital Jam. Feb. 22, 2000 at 8:18 ET: "Talking Medicine Cabinet", Video Clip: CNN.avi.

BBC Tomorrow's World, 07:30 P.M. GMT Mar. 1, 2000. Video Clip: BBC.avi.

Fox News Feb. 29, 2000. Article "Pervasive Computing Gets Personal." Online version can be accessed at: "httr)://foxnews.com/vtech/022900/bathr)c.sml".

PC Comuting. "Inventing the Future," Feb. 2000.

The Philaelphia Inquirer. Feb. 17, 2000. "Computers Could Take On More Chores without Being Told.".

The Times (London). Feb. 23, 2000: Article "Computer in Bathroom will be micro?GP".

Canadian National Post, Apr. 3, 2000. "Online medicine makes the rounds.".

ABC World News Tonight. Jul. 22, 1999. Feature "Cutting Edge" story for the evening news program. Video Clip: ABC–NEWS.ave.

* cited by examiner

ONLINE MEDICINE CABINET

BACKGROUND OF THE INVENTION

1. Technical Field

This invention relates generally to managing a person's health through a medicine cabinet with a computer system connected to the Internet. More particularly, the invention provides methods and systems for managing a person's medicine cabinet with a computer system connected to the Internet.

2. Related Information

Typical medicine cabinets merely provide a mechanism for storing a person's medication. When the medicine cabinet is located in a house in which a family resides, it is not unusual for the medicine cabinet to contain medications for different members of the household. This presents the possibility that one person may take medication inadvertently that is prescribed for a different person. Also, it is not unusual that a person will forget to have a prescription refilled until he takes the last pill of his medication.

With today's busy lifestyles, people often take their medications at the wrong time or in the wrong amount. Furthermore, people are often not aware of new warnings about adverse effects and drug interactions for different medications. It is known that one-third of emergency room visits are caused by noncompliance regarding the taking of medication.

It is also inconvenient and time consuming to arrange visits with a person's doctor or other health entity. As a result many people do not regularly consult with their doctor regarding medical problems, and do not keep their doctor up-to-date on their own medical conditions. People typically also have very little interaction with drug companies and professional care providers.

With traditional medicine cabinets having only the function of storing medication, there is a real need in the prior art for a system which can monitor a person's taking of medication, as well as providing medical alerts and prescription refills. It is also a drawback of the prior art that there is no convenient mechanism for a person to provide on a periodic basis vital signs such as blood pressure, blood sugar, cholesterol, etc. to his doctor. There is also a need in the prior art for a person to be able to view their vital signs medical records. For example, a person would benefit from being able to view his historical trend charts with regards to his vital signs. This would provide an early warning to seek medical attention which is not provided by any system or mechanism in the prior art.

SUMMARY OF THE INVENTION

The present invention provides a medicine cabinet that assists users in selecting and purchasing medication. The medicine cabinet allows the user to conveniently and efficiently manage the user's medication inventory.

In one embodiment of the present invention, by using a camera and face recognition software, the medicine cabinet can identify different persons in a household, and their special needs. For use with the medicine cabinet, the packaging for medication, such as bottles, has a label that is optically, magnetically, or electronically readable. The label contains various information about the medication. The medicine cabinet has sensors that can read these labels on the medication and store this information. The medicine cabinet also has sensors that can detect how many pills or other units of medication are contained in a bottle of medication. Thus, the medicine cabinet is able to identify each drug or medication and alert a user if that user has taken the wrong bottle out of the medicine cabinet. Furthermore, the medicine cabinet can alert the user that it is not time to take this particular medication, or that the medication was only just recently taken by this user. Thus, the medicine cabinet assists the user in avoiding not following his doctor's orders or taking the wrong medication.

The medicine cabinet also can suggest or remind a person to take medication based on environmental conditions. The medicine cabinet in one embodiment provides information such as the day's pollen count, and reminds a person to take their appropriate allergy medication. The medicine cabinet also enables users to monitor vital signs, such as blood pressure, heart rate, and cholesterol levels. Via the Internet, this information can be forwarded to the user's doctor and also via the Internet the medicine cabinet can have prescriptions refilled at a pharmacy. The medicine cabinet can detect changes in a person's vital signs that exceed predetermined thresholds and then suggest that the user make an appointment with a doctor. Via the connection to the Internet the users are able to make appointments directly through the medicine cabinet with their doctor's office. Alternatively, it is possible for the user to set up a videoconference with their doctor via the medicine cabinet. The use of video conferencing would cut down on routine doctor visits, saving time and money for consumers, doctors, and insurance companies.

In one embodiment of the present invention, the advantages of the present invention are realized by a method of aiding the user in selection of medication. In this method medication that is stored in a medicine cabinet is automatically identified. When a first item of medication has been removed from the medicine cabinet, it is also automatically identified. The medicine cabinet then automatically determines if the first item of medication that is removed from the medicine cabinet is a correct medication. The information is then presented and is indicative of a result of determining if this first item of medication is a correct medication. For identifying the medication the label is read and the number of units of medication is determined for this medication. In another embodiment, when the number of units falls below a predetermined number, a request is automatically sent to a medication supplier for a refill of this particular medication. The medicine cabinet is also able to identify a user using face recognition or fingerprint recognition software and is able to then inform the user if a selected medication is correct. The medicine cabinet also contains environmental conditions and provides information with regards to taking medication in response to the environmental conditions. The medicine cabinet keeps track of vital signs of the user as well as the amount and times when medication is taken by the user. The medicine cabinet is able to track a plurality of users and their associated medications.

In one embodiment, a radio frequency receiver is configured to read information included on radio frequency sensitive labels that are attached to items containing medication in the medicine cabinet. This information can be displayed on a display device as operatively coupled to a computer in the medicine cabinet. The computer may also be coupled to a wide area network such as the Internet.

BRIEF DESCRIPTION OF THE DRAWINGS

The present invention is illustrated by way of example and not limited in the accompanying figures in which like reference numerals indicate similar elements and in which.

DETAILED DESCRIPTION OF THE PREFERRED EMBODIMENTS

Figure 1:
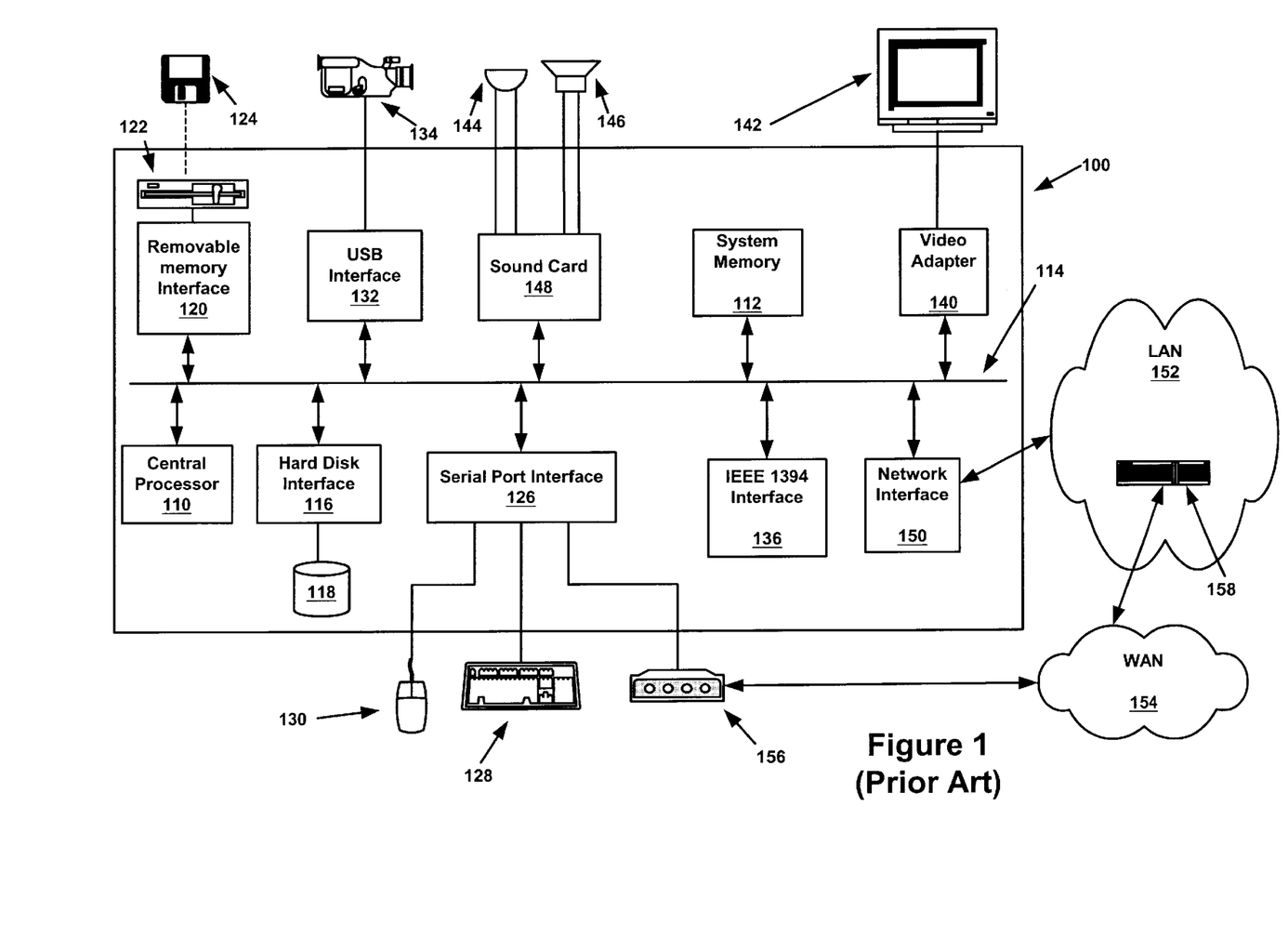
FIG. 1 shows a typical prior art workstation and communication connections.

Elements of the present invention may be implemented with computer systems, such as the system 100 shown in FIG. 1. Computer 100 includes a central processor 110, a system memory 112 and a system bus 114 that couples various system components including the system memory 112 to the central processor unit 110. System bus 114 may be any of several types of bus structures including a memory bus or memory controller, a peripheral bus, and a local bus using any of a variety of bus architectures. The structure of system memory 112 is well known to those skilled in the art and may include a basic input/output system (BIOS) stored in a read only memory (ROM) and one or more program modules such as operating systems, application programs and program data stored in random access memory (RAM).

Computer 100 may also include a variety of interface units and drives for reading and writing data. In particular, computer 100 includes a hard disk interface 116 and a removable memory interface 120 respectively coupling a hard disk drive 118 and a removable memory drive 122 to system bus 114. Examples of removable memory drives include magnetic disk drives and optical disk drives. The drives and their associated computer-readable media, such as a floppy disk 124 provide nonvolatile storage of computer readable instructions, data structures, program modules and other data for computer 100. A single hard disk drive 118 and a single removable memory drive 122 are shown for illustration purposes only and with the understanding that computer 100 may include several of such drives. Furthermore, computer 100 may include drives for interfacing with other types of computer readable media.

A user can interact with computer 100 with a variety of input devices. FIG. 1 shows a serial port interface 126 coupling a keyboard 128 and a pointing device 130 to system bus 114. Pointing device 128 may be implemented with a mouse, track ball, pen device, or similar device. Of course one or more other input devices (not shown) such as a joystick, game pad, satellite dish, scanner, touch sensitive screen or the like may be connected to computer 100.

Computer 100 may include additional interfaces for connecting devices to system bus 114. FIG. 1 shows a universal serial bus (USB) interface 132 coupling a video or digital camera 134 to system bus 114. An IEEE 1394 interface 136 may be used to couple additional devices to computer 100. Furthermore, interface 136 may configured to operate with particular manufacture interfaces such as FireWire developed by Apple Computer and i.Link developed by Sony. Input devices may also be coupled to system bus 114 through a parallel port, a game port, a PCI board or any other interface used to couple and input device to a computer.

Computer 100 also includes a video adapter 140 coupling a display device 142 to system bus 114. Display device 142 may include a cathode ray tube (CRT), liquid crystal display (LCD), field emission display (FED), plasma display or any other device that produces an image that is viewable by the user. Additional output devices, such as a printing device (not shown), may be connected to computer 100.

Sound can be recorded and reproduced with a microphone 144 and a speaker 166. A sound card 148 may be used to couple microphone 144 and speaker 146 to system bus 114. One skilled in the art will appreciate that the device connections shown in FIG. 1 are for illustration purposes only and that several of the peripheral devices could be coupled to system bus 114 via alternative interfaces. For example, video camera 134 could be connected to IEEE 1394 interface 136 and pointing device 130 could be connected to USB interface 132.

Computer 100 can operate in a networked environment using logical connections to one or more remote computers or other devices, such as a server, a router, a network personal computer, a peer device or other common network node, a wireless telephone or wireless personal digital assistant. Computer 100 includes a network interface 150 that couples system bus 114 to a local area network (LAN) 152. Networking environments are commonplace in offices, enterprise-wide computer networks and home computer systems.

A wide area network (WAN) 154, such as the Internet, can also be accessed by computer 100. FIG. 1 shows a modem unit 156 connected to serial port interface 126 and to WAN 154. Modem unit 156 may be located within or external to computer 100 and may be any type of conventional modem such as a cable modem or a satellite modem. LAN 152 may also be used to connect to WAN 154. FIG. 1 shows a router 158 that may connect LAN 152 to WAN 154 in a conventional manner.

It will be appreciated that the network connections shown are exemplary and other ways of establishing a communications link between the computers can be used. The existence of any of various well-known protocols, such as TCP/IP, Frame Relay, Ethernet, FTP, HTTP and the like, is presumed, and computer 100 can be operated in a client-server configuration to permit a user to retrieve web pages from a web-based server. Furthermore, any of various conventional web browsers can be used to display and manipulate data on web pages.

The operation of computer 100 can be controlled by a variety of different program modules. Examples of program modules are routines, programs, objects, components, data structures, etc., that perform particular tasks or implement particular abstract data types. The present invention may also be practiced with other computer system configurations, including hand-held devices, multiprocessor systems, microprocessor-based or programmable consumer electronics, network PCS, minicomputers, mainframe computers, personal digital assistants and the like. Furthermore, the invention may also be practiced in distributed computing environments where tasks are performed by remote processing devices that are linked through a communications network. In a distributed computing environment, program modules may be located in both local and remote memory storage devices.

Figure 2:
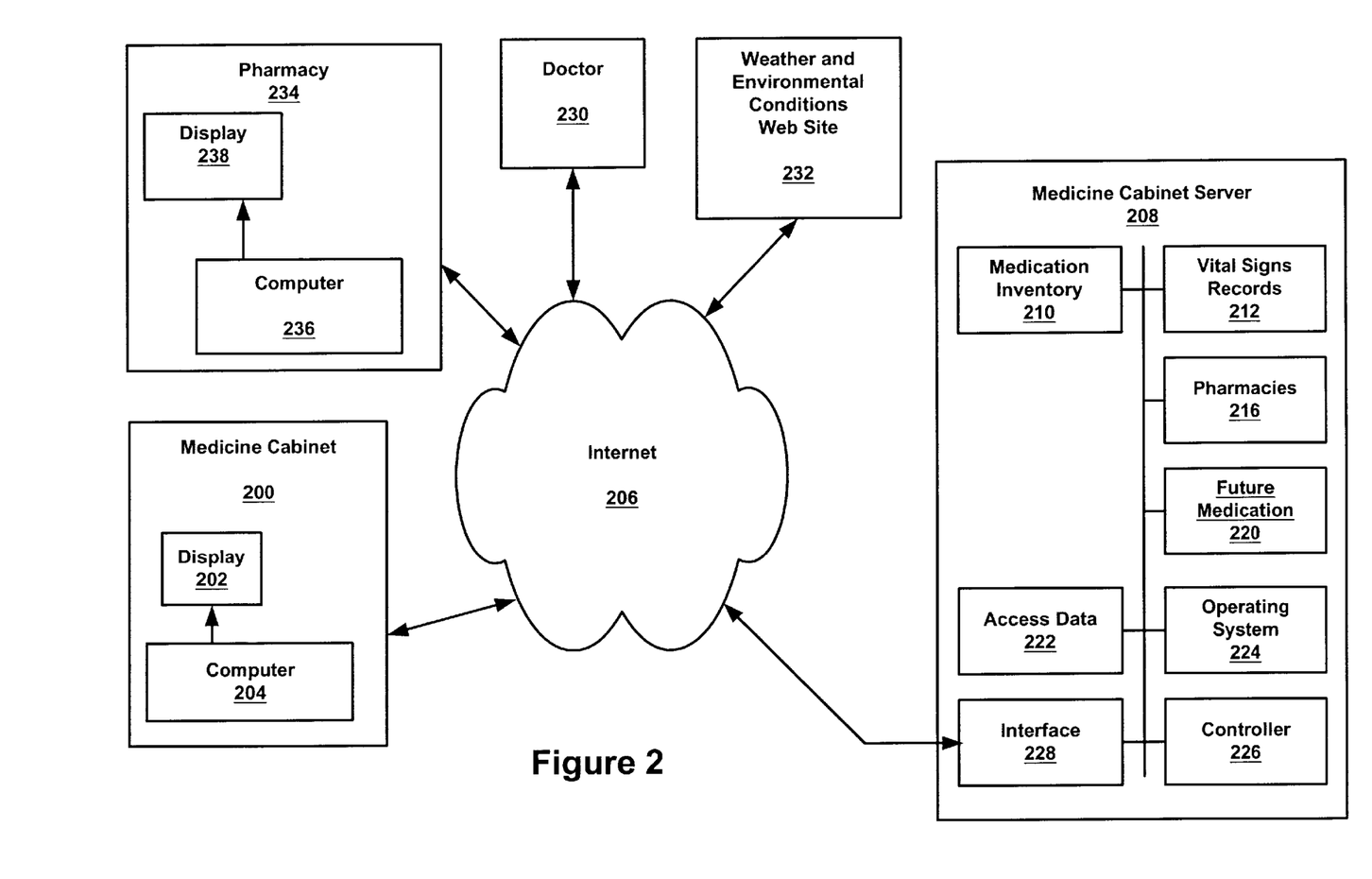
FIG. 2 illustrates a computer network system they can be used to select and purchase medication in accordance with an embodiment of the invention.

FIG. 2 illustrates a system for managing medication in accordance with an embodiment of the invention. A medicine cabinet 200 includes a computer 204, a display 202 and may be connected to a wide area network, such as the Internet 206. The structure of medicine cabinet 200 will be described in greater detail with reference to FIGS. 3, 4 and 5. Furthermore, the operation of medicine cabinet 200 and the remaining elements shown in FIG. 2 will be described in greater detail with reference to FIGS. 6–7.

Medicine cabinet 200 may store and transmit information relating to the medication acquired by a user. In one embodiment of the invention, the information is transmitted through the Internet 206 to a medicine cabinet server 208. Medicine cabinet server 208 may store information for variety of different users and may be implemented with a variety of conventional components. Medicine cabinet server 208 includes a medication inventory memory module 210 that may be used to store a user's medication information. The user's vital signs records, for example blood pressure measurements, temperature, pulse rates, etc., may be store in a vital signs records memory module 212. Additional medication information may also be stored in medicine cabinet server 208. For example the identification of pharmacies may be stored in pharmacy memory module. Medication that the user wishes to purchase in the future may be stored in a future medication list memory module 220.

Access to medicine cabinet server 208 may be controlled by information contained in access data module 222. A variety of different methods may be used to control access to medicine cabinet server 208. In one embodiment of the invention, the user is required to enter a personal identification number (PIN) before accessing medicine cabinet server 208. In another embodiment of the invention, an access code is read from a smart card to permit access to medicine cabinet server 208. The overall operation of medicine cabinet server 208 may be governed by an operating system program 224 in conjunction with a controller 226. Operating system program 224 and controller 226 may be implemented with a variety of conventional programs and electronic components that are well known to those skilled in the art. Medicine cabinet server 208 also includes an interface 228, such as a modem, that allows medicine cabinet server 208 to communicate with the Internet 206.

FIG. 2 illustrates an embodiment in which medicine cabinet server 208 is separated from medicine cabinet 200. Of course, one or more of the components shown in medicine cabinet server 208 may be included in medicine cabinet 200.

A variety of websites may be connected to Internet 206. FIG. 2 shows a doctor's office web site 230 that allows consumers to be able to setup videoconferences with their doctor or other relevant medical personnel. A weather and environmental conditions web site 232 is also shown. The weather and environmental conditions web site 232 may provide information to medicine cabinet 200 to aid in the selection of medication in a manner that will be described in detail below. Of course, numerous additional websites may also be included to allow users to purchase medication and obtain information. In addition to websites, the system shown in FIG. 2 also includes a pharmacy 234 where medications can be refilled. The pharmacy 234 will typically include at least a computer 236 and a display 238. The operation of these components will be in described in detail below.

Figure 3:
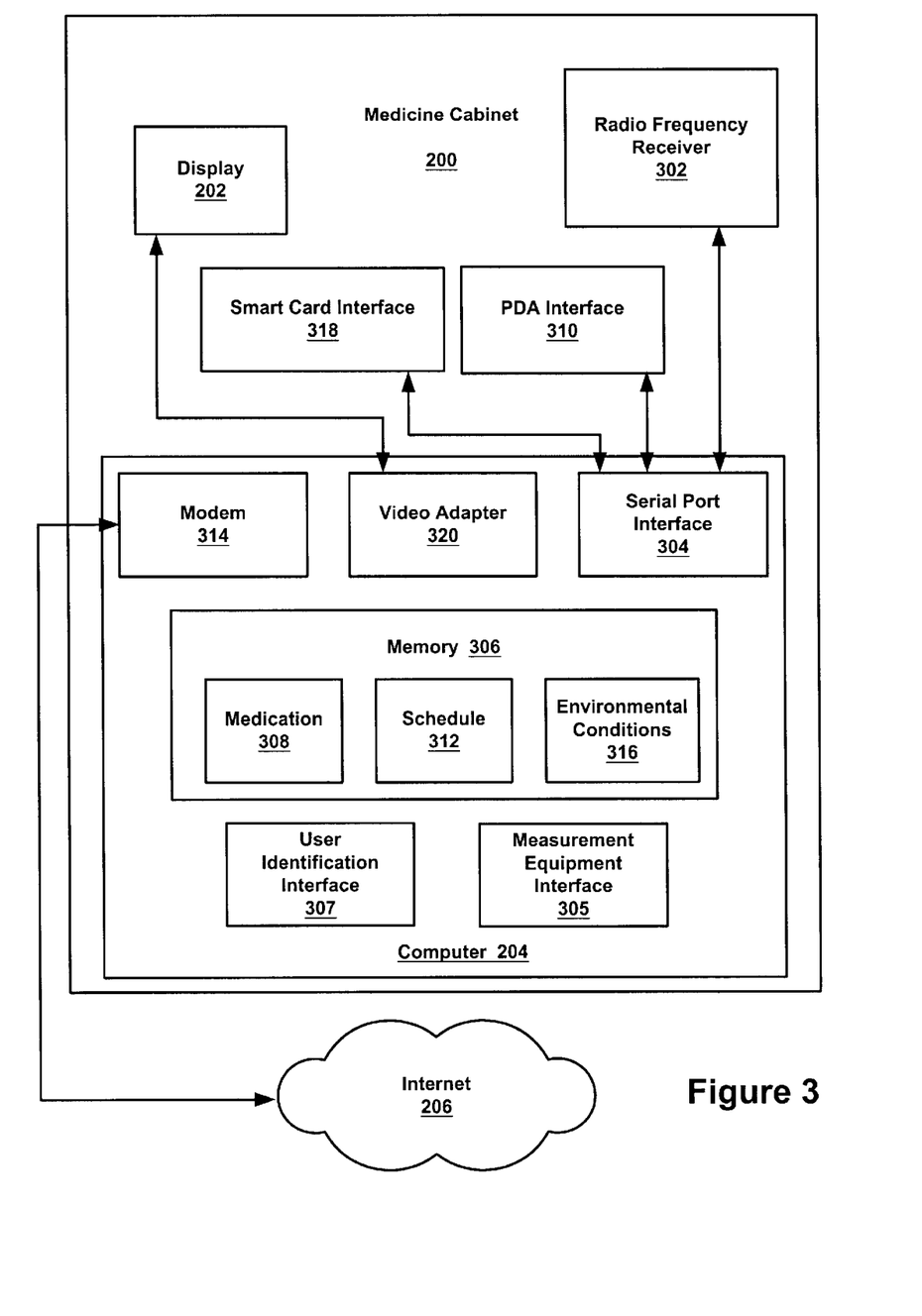
FIG. 3 is a schematic diagram of a medicine cabinet.

FIG. 3 shows a schematic diagram of a medicine cabinet in accordance with one embodiment of the invention. A radio frequency (RF) receiver 302 scans RF labels or sensors that are embedded in packaging for the medication. The information obtained from radio frequency receiver 302 is transmitted to a serial port interface 304. Computer 204 stores the information obtained from serial port interface 304 in a medication section 308 of a memory 306. Of course, the present invention may be implemented with other labels or sensors such as Electronic Product Code (EPC) labels. Furthermore, RF receiver 302 may be replaced with a receiver operating at a different frequency, an optical reader or another reader capable of reading labels or sensors. One example of such a system is the Texas Instruments' "Tag-It-RFID" tags and readers. The RFID tag in one embodiment is coded for accessing a database that contains relevant data, such as type of medication, etc. Or course, it is possible to code the RFID tag with other information, or with data relevant to the associated medication.

Medicine cabinet 200 also may include a personal digital assistant (PDA) interface 310 coupled to serial port interface 304. The user may store schedule information for taking medication in a PDA and enter the information into a schedule section 312 of memory 306 via PDA interface 310. Medicine cabinet 200 also includes a modem 314 coupling computer 204 to the Internet 206. Information such as environmental conditions in one or more geographic areas may be retrieved from Internet 206 and stored in the environmental section 316 of memory 306. A video adapter 320 may be used to cause display 202 to display information stored in memory 306 or retrieved from the Internet 206. Additional uses for the information stored in memory 306 and information retrieved from the Internet 206 will be described below.

Medicine cabinet 200 may also include a smart card interface 318 that may be used to couple a smart card (not shown) to computer 204. A smart card may include information that identifies the user, identifies a medication used by the user or other information to be stored in memory 306 or in medicine cabinet server 208.

One skilled in the art will appreciate that the present invention can be implemented with several medicine cabinets. In one embodiment, each medicine cabinet has separate RF receivers for identifying medication and each of the RF receivers may be coupled to a common computer. Alternatively, each medicine cabinet may include a computer and the computers may be coupled together.

Figure 4:
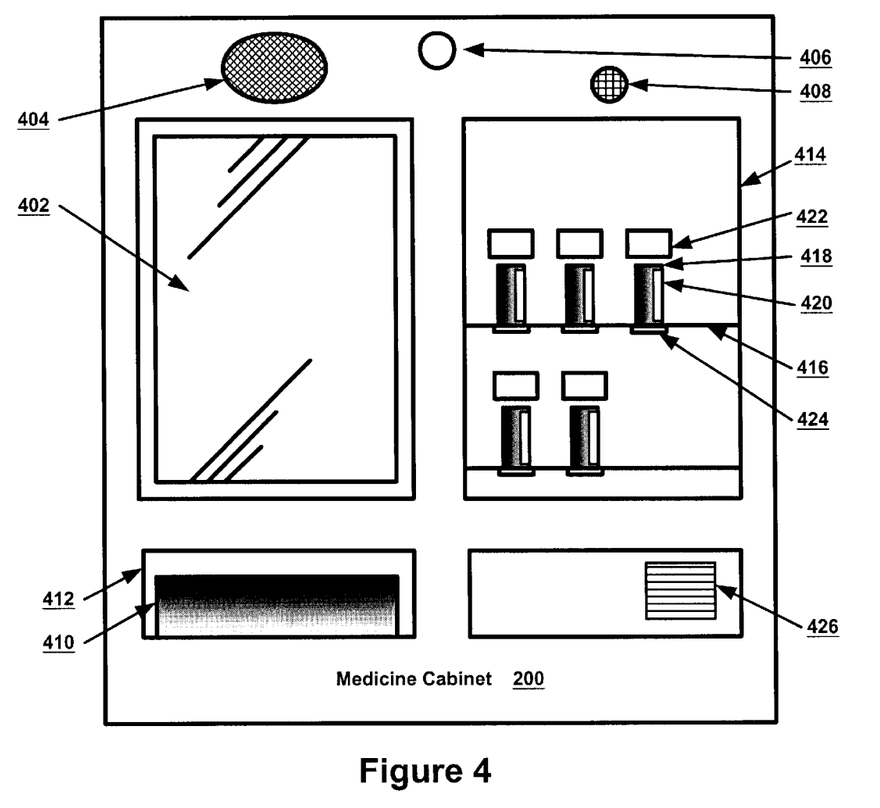
FIG. 4 is another schematic diagram of the medicine cabinet.

FIG. 4 is a schematic front view of the medicine cabinet 200. This view shows the various elements of the medicine cabinet 200 as seen by a user. When a user stands in front of the medicine cabinet 200 a video camera 406 in conjunction with the face recognition software in the computer of the medicine cabinet 200 identifies the user. An example of such a system is the "FaceIt" faced recognition software from Visionics. As described above, a database stores medications that are associated with this particular user. Such medications may be one or all of the medications 418 depicted in FIG. 4. Each of the medications 418 has a label 420. The medicine cabinet 200 has at least one sensor 422, which reads the label 420 on the medication 418. A gravity weight sensor 424 is utilized to determine the amount of medication which is contained in the packaging of the medication 418. As explained above all this information is kept in a database or memory of the medicine cabinet 200 or at a remote server 208. FIG. 4 depicts a sensor 422 associated with each medication 418. Other various arrangements are possible, such as using one sensor for detecting all of the medication contained in the medicine cabinet. The medication 418 in its packaging rests on the gravity weight sensor 424 which is attached to a shelf 416, for example, in a medication storage area 414 of the medicine cabinet 200. As an alternative or in conjunction with the video camera 406 the medicine cabinet 200 may have fingerprint detection equipment 426, which in conjunction with fingerprint recognition software can be used to identify the user.

The medicine cabinet 200 is also equipped with a microphone 408 and a speaker 404. The display 402 of the medicine cabinet 200 in one embodiment is a touch screen flat panel display. All information that is provided to the user can be displayed on the display 402 and/or audibly by the speaker 404 using speech synthesis software. In addition, the user can set up video conferencing using the video camera 406, the microphone 408, the speaker 404, and the display 402. The medicine cabinet 200 as described above is connected to the Internet and thus provides for video conferencing, or simply an audio connection using the microphone 408 and the speaker 404.

Figure 5:
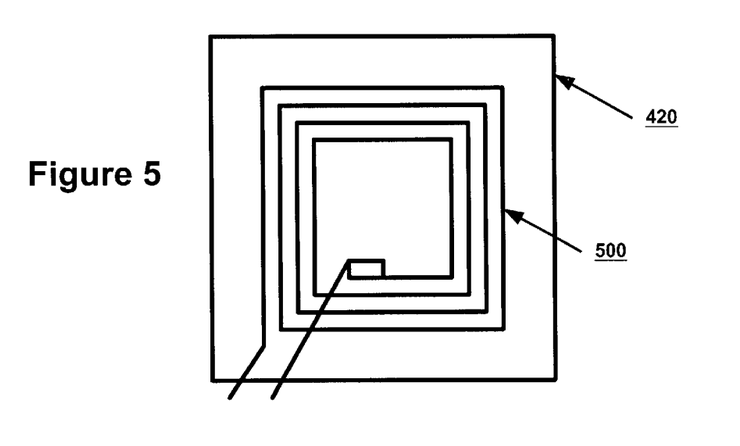
FIG. 5 depicts a label used on packaging for medication.

FIG. 5 depicts one example of a label 420 which has a radio frequency coil 500. Such labels are well known in the art and are used for identifying different types of items. It is also envisioned that various other types of labels and detection equipment such as bar codes with optical readers or magnetic strips with magnetic readers can be used with the present invention.

It can be appreciated that the various features of the medicine cabinet of the present invention can be utilized in various selective combinations. For example, the medicine cabinet of the present invention can be a stand-alone unit which is not connected to the Internet, but which still has a database and can still detect when a user removes the wrong medication, or the correct medication at the wrong time from its storage area in the medicine cabinet. Such a stand-alone medicine cabinet can also still record and store vital signs of a user. For example, the medicine cabinet 200 in FIG. 4 has a compartment 412 in which is stored blood pressure equipment 410. In addition vital sign measurements of the user, such as temperature can be input via the touch screen flat panel display 402. However, it is advantageous for the medicine cabinet 200 to be connected to a local area network and/or a wide area network such as the Internet.

Figure 6:
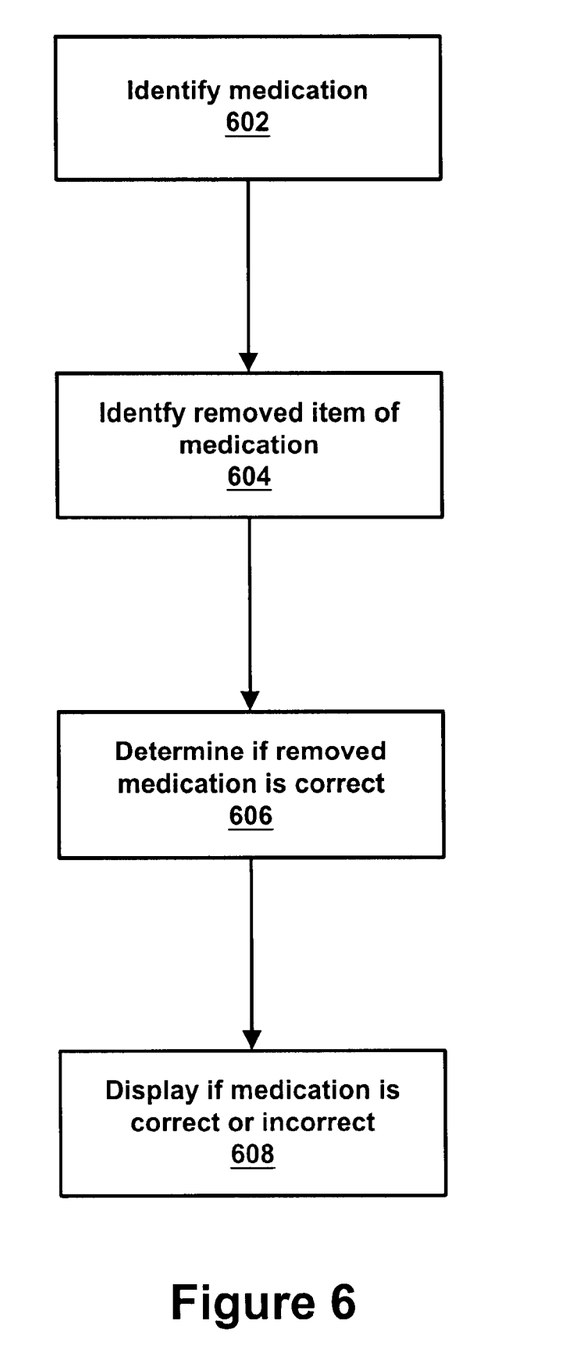
FIG. 6 illustrates a method for assisting a user in selecting medication.

FIG. 6 depicts in general the method of the present invention. In a first step 602 medication stored in the medicine cabinet is automatically identified. When a user removes a first item of medication from the medicine cabinet the medicine cabinet automatically identifies this first item of medication in step 604. In step 606 the medicine cabinet then automatically determines if the first item of medication removed from the medicine cabinet is a correct medication, that is, if this medication is associated with the current user and if it is time for the current user to be taking this medication. In step 608 the medicine cabinet then presents information to the user indicative of a result of determining if the first item of medication is the correct medication.

Figure 7:
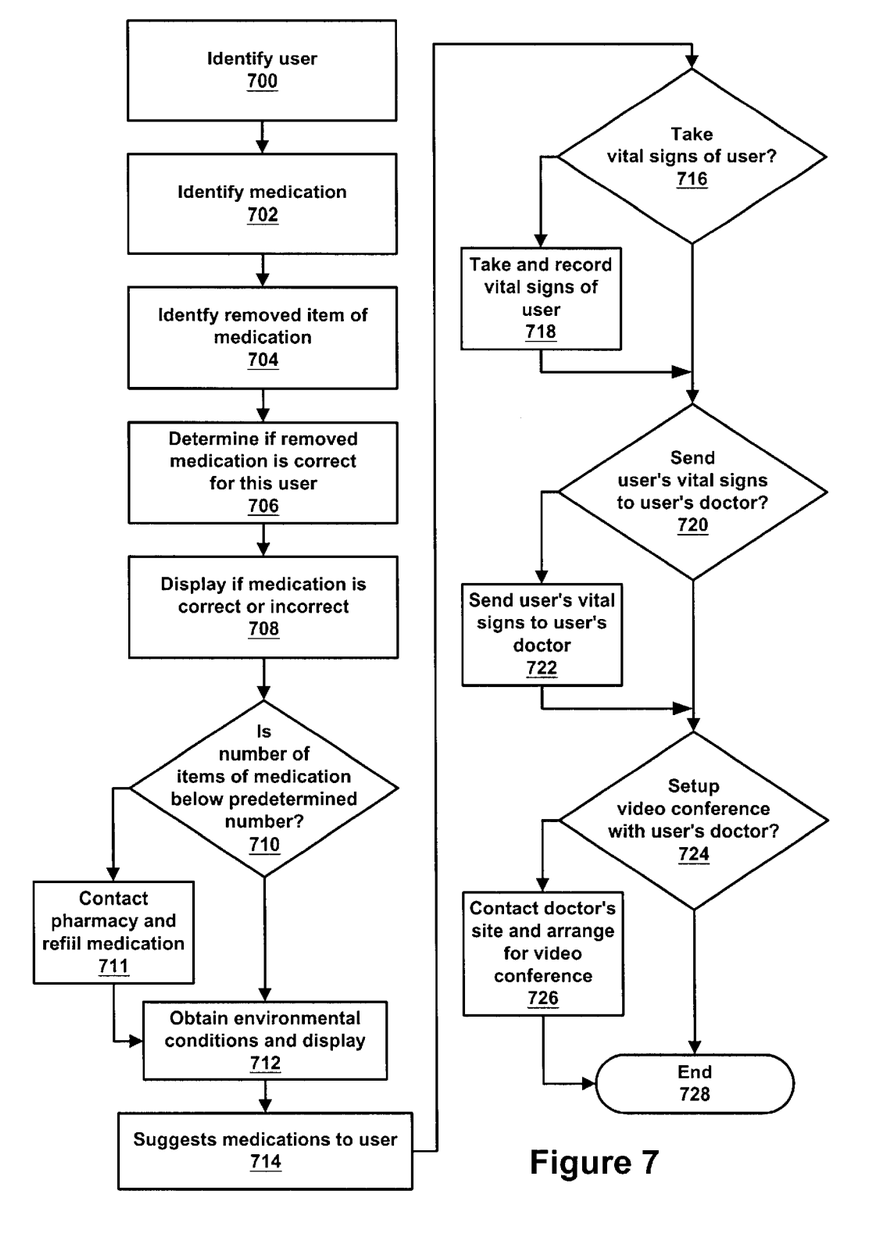
FIG. 7 illustrates a further method of the present invention.

FIG. 7 shows a more detailed flowchart of a medicine cabinet with various features. In first step 700 a user standing in front of the medicine cabinet is identified. Such identification may take place via a video camera with face recognition software and/or fingerprint identification equipment and fingerprint recognition software. In step 702 the medicine cabinet automatically identifies medication stored in the medicine cabinet. It is to be understood that such automatic identification can take place on a periodic basis or may take place only at certain defined points in time. Thus, it is not necessary, for example, that every time a user approaches the medicine cabinet that the medicine cabinet identifies all medications stored in the medicine cabinet. In a step 704 the medicine cabinet automatically identifies the first item of medication that has been removed from the medicine cabinet by the user. In step 706 the medicine cabinet determines if this is the correct medication for this user. In step 708 the information is then presented on the display of the medicine cabinet. If the medicine cabinet has detected that the number of items of medication in the packaging of a particular medication has fallen below a predetermined number, then the medicine cabinet automatically refills the prescription (see steps 710 and 711). Alternatively, the medicine cabinet may alert the user via the display device and await the user's instructions with regards to refilling the prescription. In step 712 the medicine cabinet via the Internet downloads current weather and environmental condition data which is displayed on the display device of the medicine cabinet. In step 714 the medicine cabinet suggests to the user that certain medications, for example allergy medications, be taken because of the current environment conditions.

In step 716 the medicine cabinet is either instructed or requests of the user that vital signs of the user be taken. The equipment for taking vital signs which is attached to the medicine cabinet is used and the data is then stored in the database either in the medicine cabinet or at a remote location (see step 718). In step 720 the medicine cabinet determines if the vital sign records, that is the data stored in step 718, is to be sent to the user's doctor or other health organization. Typically this would be accomplished via the network attached to the medicine cabinet, such as the Internet. In this step 720 the medicine cabinet may either automatically forward the information, alert the user that the information should be forwarded to the doctor based on certain predetermined criteria, or send the data to the doctor in response to instructions that have been input by the user. If the data is to be sent to the doctor, then in step 722 this data is forwarded to, for example, a doctor's website via the Internet. Also, if instructed by the user or based on other criteria, the medicine cabinet can initiate a videoconference with the doctor or other health provider in steps 724 and 726. Step 728 terminates the session with the medicine cabinet. As stated above, it is to be understood that various combinations of the inventive features can be utilized in a medicine cabinet.

As service delivery channel, the medicine cabinet of the present invention can be used as a service delivery channel for people suffering from chronic conditions, such as diabetes, hypertension, etc. A custom set of monitoring devices are integrated with a respective medicine cabinet to support such specific medical condition. A remote third-party service provider can provide what is termed "24×7" support, including live specialist support. A person can subscribe to such a service by paying a monthly service fee.

It is very advantageous to use an embodiment in which the medicine cabinet is connected to the Internet. With the advent of the Internet there has been an explosion of healthcare information. It is known that two-thirds of Internet users use the Web on the Internet to search for health information. However, there are two important sides to healthcare of a user. The first category includes determining potential side effects of a given drug or scheduling an office visit to a user's physician. The second category includes the actual taking of medication or measuring vital signs. Proper healthcare requires a continuous interplay of information exchange and physical care.

The medicine cabinet of the present invention provides for both the informational and physical aspects of a user's healthcare. This includes routine physical care, such as reminding the user and making sure the user takes the right medication as well as tracking vital signs of the user. It also includes downloading of personalized up-to-date health information, and the ability to interact online with physicians, pharmacists, and other professional healthcare providers. The medicine cabinet of the present invention is able to inventively provide these features and overcome the drawbacks of the prior art by utilizing software recognition of the user, such as face recognition software and/or fingerprint recognition software, radio frequency identification based smart labels on drug products, vital sign monitoring equipment, and voice synthesis software.

While the present invention has been described in connection with the illustrated embodiments, it will be appreciated and understood that modifications may be made without departing from the true spirit and scope of the invention. For example, the present invention can used in a medication cart that is moveable to various locations in a hospital or other medical facility. The present invention is thus embodiable in various devices that are useable in a wide variety of locations. Furthermore, other methods and systems can be used to determine the number of items of medication in a particular container, or to track the removal thereof over a period of time. For example, an initial number of items of medication can be recorded for a new prescription, and the current number of items is periodically updated as the medication is taken by a person.

What is claimed is:

1. A method of tracking use of medications, comprising the steps of:
    (a) automatically identifying medication stored in a medicine cabinet by reading labels associated with the medications, the labels at least respectively identifying the medications; and
    (b) automatically detecting use of the medications in the medicine cabinet by detecting removal of a respective medication from the medicine cabinet and by automatically detecting changes in a quantity of items of medication of the respective medication.

2. The method of claim 1, wherein the method further comprises automatically identifying a first item of medication that has been removed from the medicine cabinet, and automatically determining if the first item of medication removed from the medicine cabinet is a correct medication.

3. The method of claim 2, wherein the method further comprises presenting information indicative of a result of determining if the first item of medication is a correct medication.

4. The method of claim 1, wherein the method further comprises, when the number of units of medication falls below a predetermined number, automatically sending a request to a medication supplier for a refill of the first item of medication.

5. The method of claim 1, wherein the method further comprises identifying a user, and determining if an item of medication, which has been removed by the user from the medicine cabinet, is associated with the identified user.

6. The method of claim 5, wherein the method further comprises presenting to the user information regarding at least one of the removed medication is a correct medication for the user, a correct dosage of the medication, and a correct time for taking the medication.

7. The method of claim 5, wherein the user is identified using a face recognition system.

8. The method of claim 5, wherein the user is identified using a finger print recognition system.

9. The method of claim 1, further including the steps of:
    determining environmental conditions; and
    providing information regarding taking medication in response to the environmental conditions.

10. The method of claim 9, wherein the medicine cabinet is coupled to a computer network, and wherein the environmental conditions are retrieved from a source connected to the computer network.

11. The method of claim 1, wherein the method further comprises the steps of:
    identifying items of medication stored in the medicine cabinet during a first time period by scanning labels attached to the items of medication in the medicine cabinet;
    identifying items of medication stored in the medicine cabinet during a second time period by scanning labels attached to the items of medication in the medicine cabinet; and comparing information obtained during the first time period to information obtained during the second time period and providing therefrom information regarding changes in stored medication.

12. The method of claim 1, wherein the method further comprises presenting information relative to the medications visually on a display of the medicine cabinet.

13. The method of claim 1, wherein the method further comprises presenting information relative to the medications audibly via an audio system of the medicine cabinet.

14. The method of claim 1, wherein respective medications of a plurality of medications are identified for respective users of plurality of users.

15. The method of claim 1, wherein the method further includes executing a software algorithm that recommends alternative and/or additional medication as a function of at least one predetermined condition.

16. The method of claim 15, wherein the at least one predetermined condition is an environmental condition.

17. A method of aiding a user in the selection of medication, comprising the steps of:
   a. identifying a respective user of a plurality of users;
   b. automatically identifying medication stored in a medicine cabinet by reading labels associated with items of medication, a respective label at least identifying respective medication, and by determining a number of units of medication of respective medication;
   c. automatically identifying a first item of medication that has been removed from the medicine cabinet, and automatically detecting changes in the number of units of said respective medication;
   d. automatically determining if the first item of medication removed from the medicine cabinet is a medication associated with the respective user; and
   e. displaying information indicative of a result of determining if the first item of medication is associated with the respective user.

18. The method of claim 17, wherein the method further comprises, when the number of units of medication falls below a predetermined number, automatically sending a request to a medication supplier for a refill of the first item of medication.

19. The method of claim 17, wherein the method further comprise presenting to the respective user information regarding at least one of a correct dosage of the medication, and a correct time for taking the medication.

20. The method of claim 17, wherein the user is identified using at least one of a face recognition system and a fingerprint recognition system.

21. The method of claim 17, wherein the medicine cabinet is coupled to a computer network, and wherein environmental conditions are downloaded from a source connected to the computer network, and wherein information regarding taking medication is displayed in response to the environmental conditions.

* * * * *